US006792640B2

(12) United States Patent
Lev

(10) Patent No.: US 6,792,640 B2
(45) Date of Patent: Sep. 21, 2004

(54) AUTOMATIC ELECTRIC TOOTHBRUSH

(75) Inventor: Mordechai Lev, Northville, MI (US)

(73) Assignee: HoMedics, Inc., Commerce Township, MI (US)

( * ) Notice: Subject to any disclaimer, the term of this patent is extended or adjusted under 35 U.S.C. 154(b) by 302 days.

(21) Appl. No.: 09/946,425

(22) Filed: Sep. 5, 2001

(65) Prior Publication Data

US 2003/0000032 A1 Jan. 2, 2003

Related U.S. Application Data

(60) Provisional application No. 60/302,010, filed on Jun. 29, 2001.

(51) Int. Cl.[7] .............................................. A61C 17/22
(52) U.S. Cl. ........................ 15/28; 15/22.1; 200/42.01; 200/61.42; 200/61.58 R; 200/332.3; 200/511
(58) Field of Search ................................ 15/22.1–22.4, 15/23, 28; 200/42.01, 52 R, 61.41, 61.42, 61.58 R, 61.85, 332.3, 511, 512, 600

(56) References Cited

U.S. PATENT DOCUMENTS

| | | | |
|---|---|---|---|
| 3,848,336 A | 11/1974 | Copeland ...................... | 433/99 |
| 3,859,684 A | 1/1975 | Moskwinski ................... | 15/23 |
| 3,939,599 A | 2/1976 | Henry et al. .................. | 433/99 |
| 4,192,035 A | 3/1980 | Kuris .......................... | 15/22.1 |
| 4,458,702 A | 7/1984 | Grollimund .................. | 132/322 |
| 4,882,801 A | 11/1989 | Benz ............................. | 15/23 |
| 5,282,291 A | 2/1994 | Spieler et al. ............. | 15/167.1 |
| 5,453,644 A | 9/1995 | Yap et al. .................... | 307/116 |
| 5,502,861 A | 4/1996 | Spieler et al. ............. | 15/167.1 |
| 5,577,285 A | 11/1996 | Drossler ...................... | 15/22.1 |
| 5,625,916 A | 5/1997 | McDougall .................... | 15/28 |
| 5,680,666 A | 10/1997 | Ra .............................. | 15/97.2 |
| 5,836,030 A | 11/1998 | Hazeu et al. ................. | 15/22.1 |
| 5,901,397 A | 5/1999 | Hafele et al. ................ | 15/22.1 |
| 6,067,688 A | 5/2000 | West ............................ | 15/311 |
| 6,178,579 B1 | 1/2001 | Blaustein et al. ............. | 15/28 |
| 6,189,693 B1 | 2/2001 | Blaustein et al. ........ | 206/362.2 |
| 6,195,828 B1 | 3/2001 | Fritsch ....................... | 15/22.1 |
| 6,237,178 B1 | 5/2001 | Krammer et al. ............ | 15/22.1 |
| 6,308,358 B2 | 10/2001 | Gruber et al. ............... | 15/22.1 |
| 6,308,359 B2 | 10/2001 | Fritsch et al. ................ | 15/22.1 |
| 6,327,734 B1 | 12/2001 | Meginniss, III et al. ...... | 15/105 |

Primary Examiner—Mark Spisich
(74) Attorney, Agent, or Firm—Brooks Kushman P.C.

(57) ABSTRACT

An electric, motorized toothbrush includes a switch that has an "automatic" position. The "automatic" mode provides for intermittent motorized operation, which is dependent upon application of an external force. Various embodiments allow for the force to be exerted either on the toothbrush handle, such as when it is gripped by the user, or on the brush head itself—e.g., when the brush head contacts the user's teeth. A substantially hollow housing allows for placement of battery, motor, gears, and linkages to facilitate motorized movement of the brush head.

1 Claim, 6 Drawing Sheets

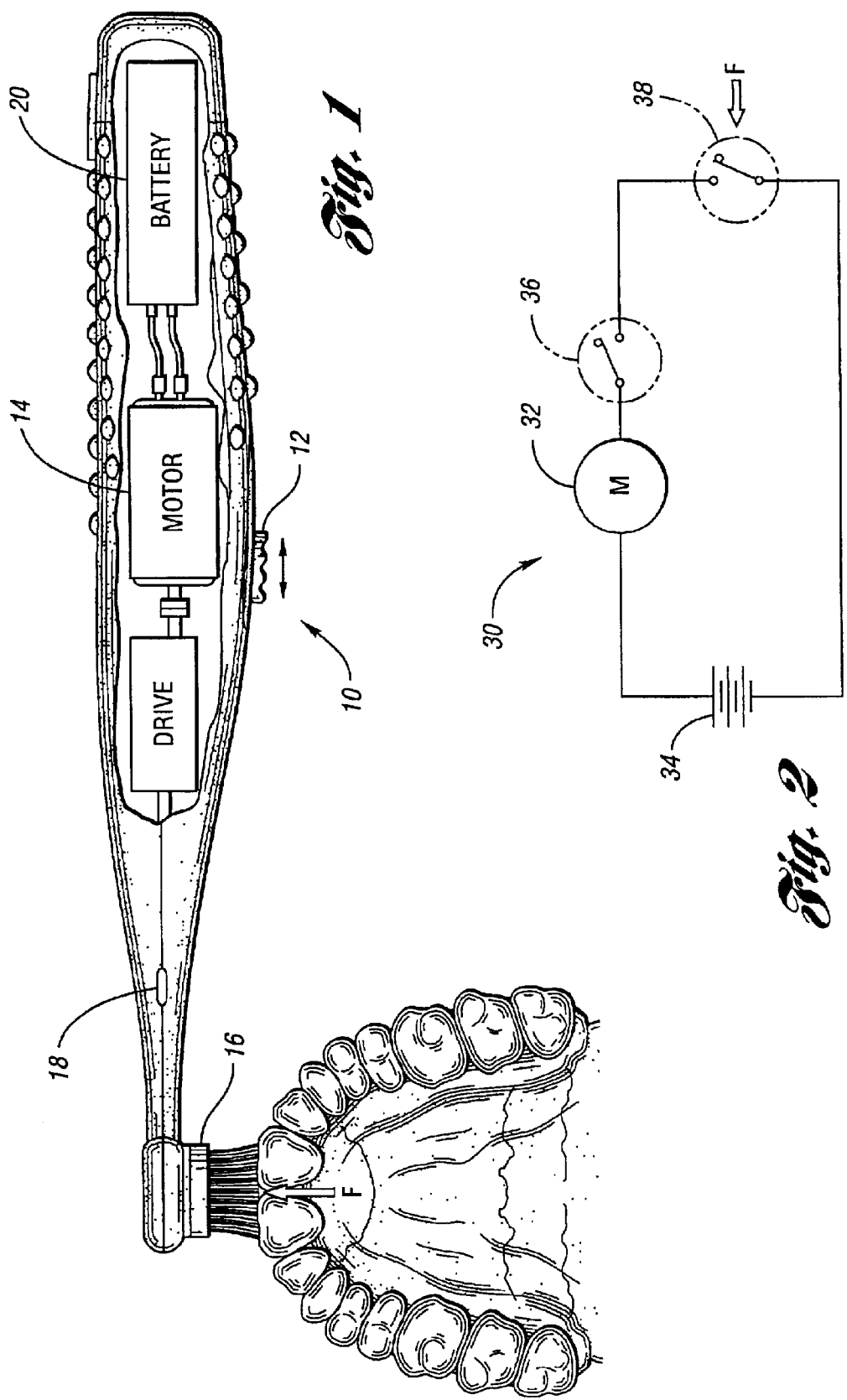

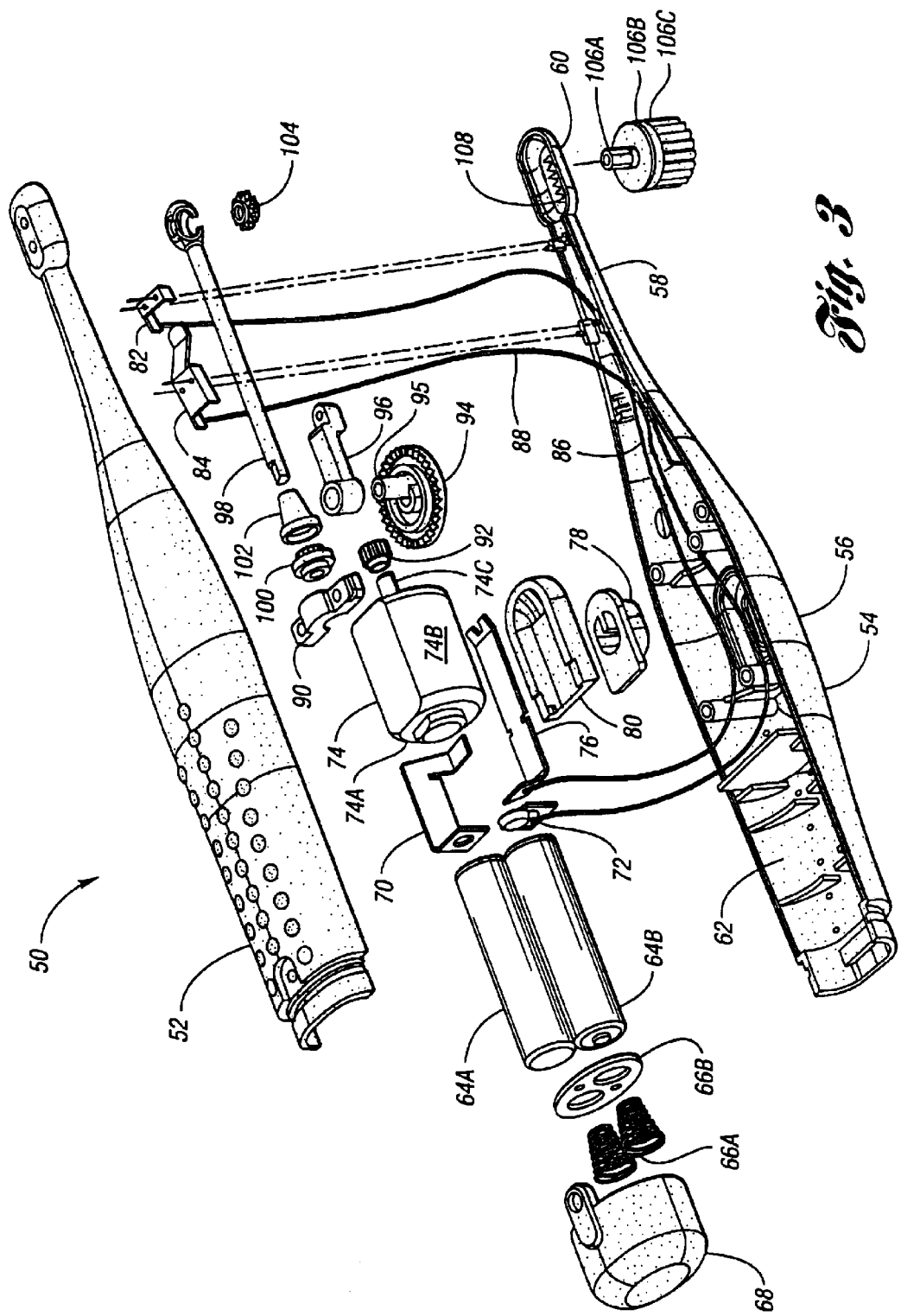

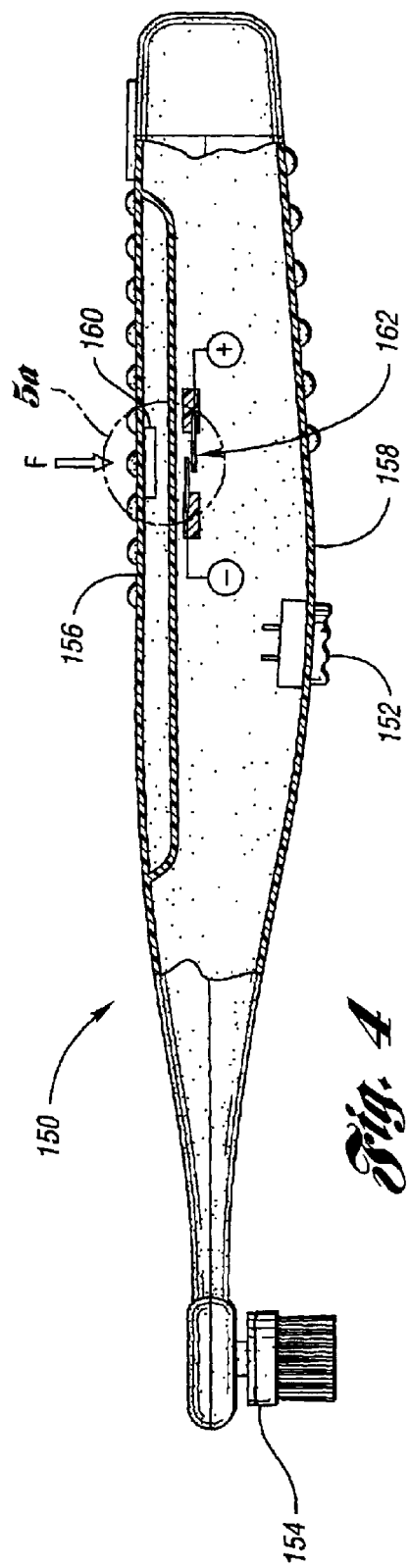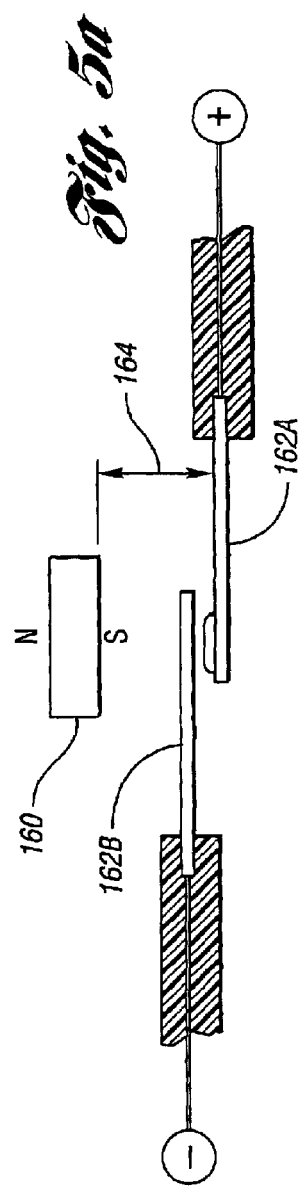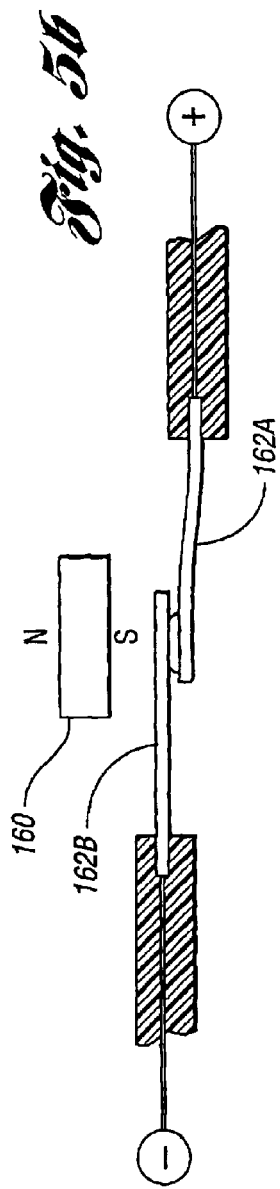

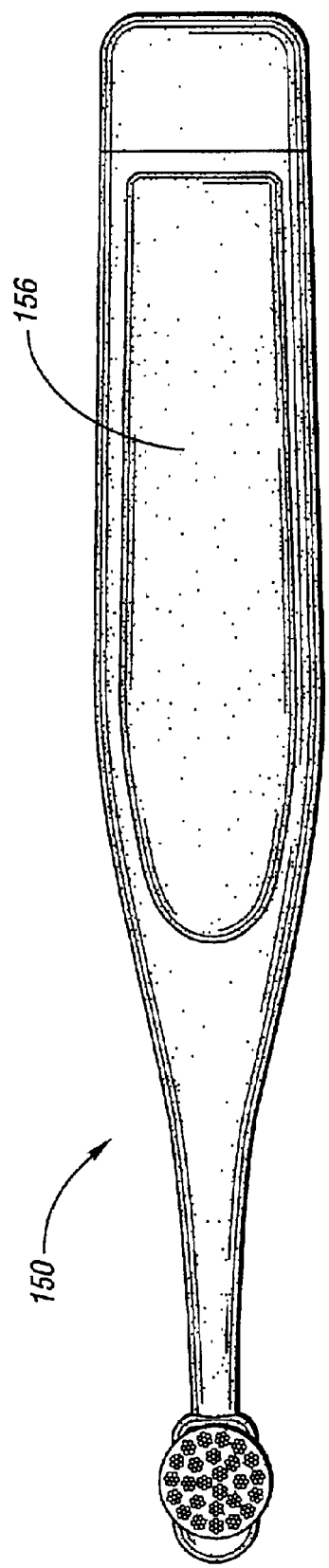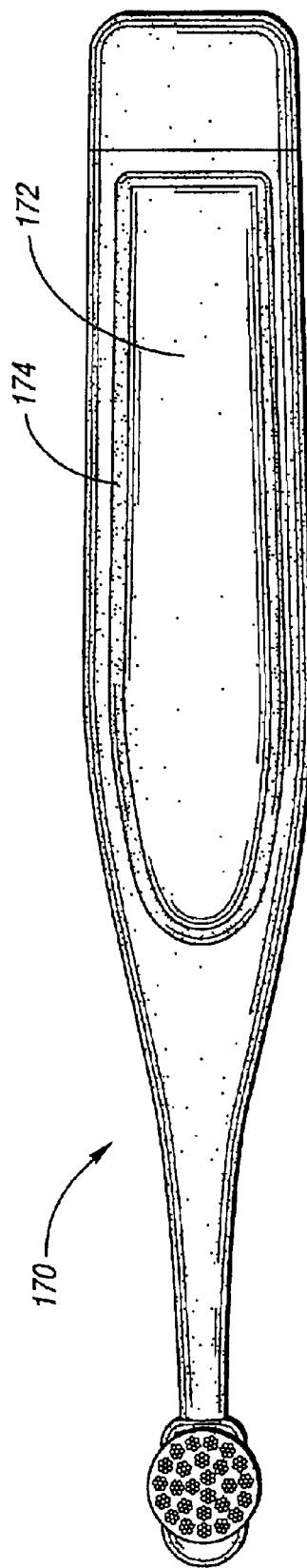

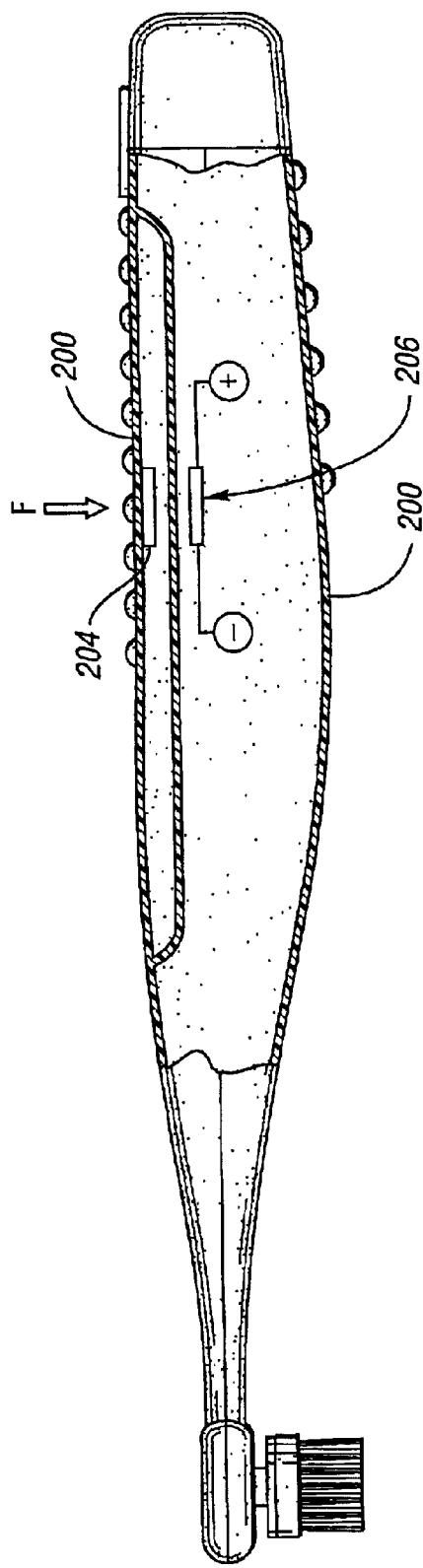
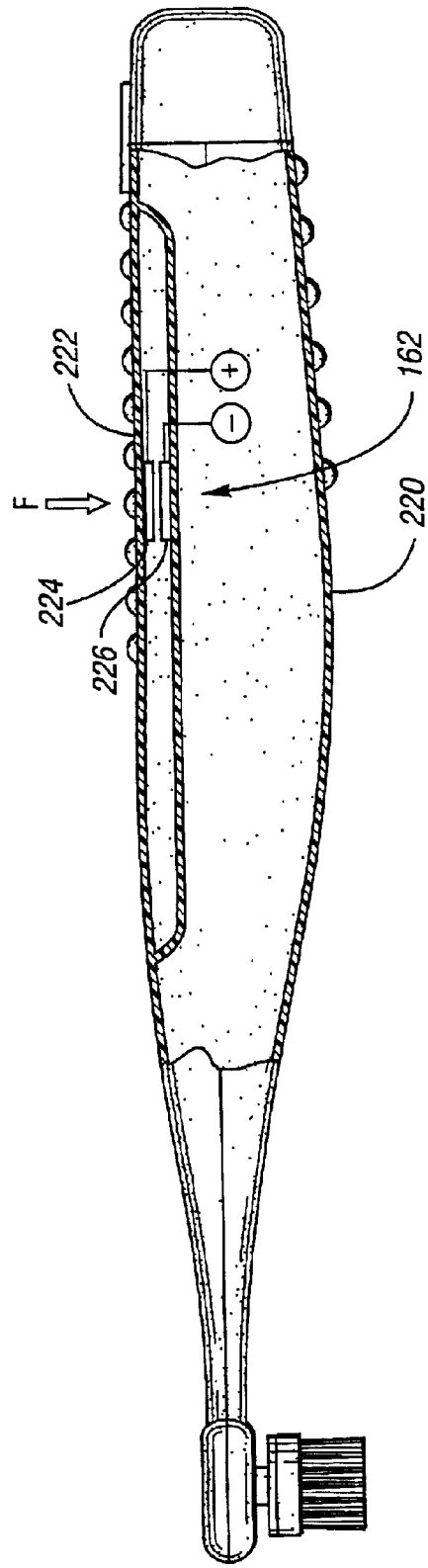

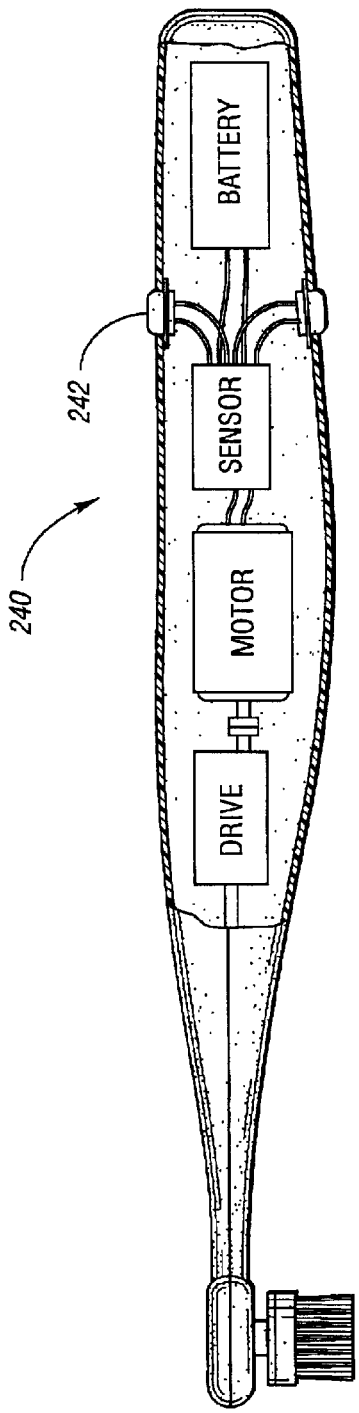
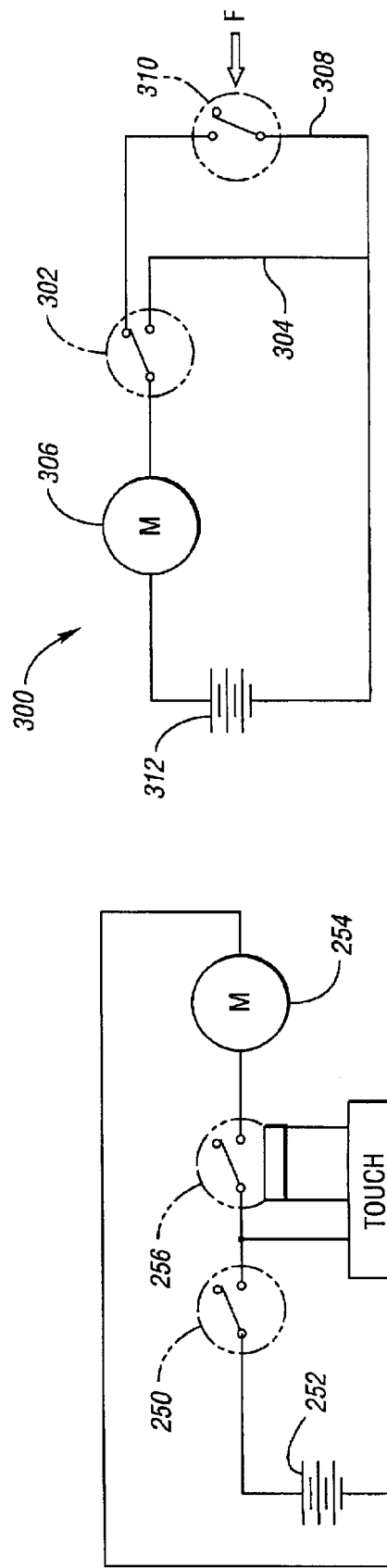
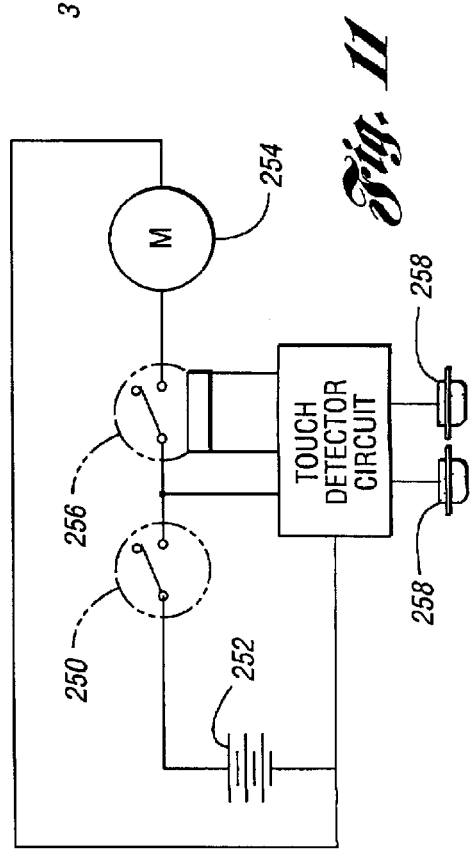

AUTOMATIC ELECTRIC TOOTHBRUSH

CROSS-REFERENCE TO RELATED APPLICATION

This application claims the benefit of U.S. provisional application serial No. 60/302,010, filed Jun. 29, 2001.

BACKGROUND OF THE INVENTION

1. Field of the Invention

The present invention relates to an electric toothbrush with a multi-position switch allowing for an automatic mode of operation.

2. Background Art

Use of electric, motorized toothbrushes used as an aid in cleansing teeth is well known. Typically these toothbrushes employ rotating, reciprocating, or oscillating motion, or a combination thereof, to effectuate the cleaning process.

A feature commonly found on these toothbrushes is a sliding on/off switch located on or near the handle portion of the toothbrush. The primary feature of such a switch is that it remains either in the "on" position or the "off" position until the user manually changes it. With such a switch, the user has a limited number of choices. The toothbrush motor can be engaged prior to the brush head being placed in the mouth, or the user can wait until the brush head is placed within the mouth before engaging the motor. Both of these choices have inherent undesirable consequences.

When the user engages the motor prior to placing the brush head in the mouth, the rapid movement of brush head may cause the toothpaste to be shaken off the bristles. Conversely, if the user waits until the brush head is inside the mouth, and in particular in contact with the teeth, it may be difficult to engage the switch, depending on its position relative to the user's hand.

Accordingly, it is desirable to provide an improved electric, motorized toothbrush that overcomes the above referenced shortcomings of prior art toothbrushes, by providing an automatic mode of operation.

DISCLOSURE OF THE INVENTION

The present invention provides an electric, motorized toothbrush that can be used in an "automatic" mode. The automatic mode allows the user to insert the brush head into the user's mouth before the motor is engaged and the brush head starts moving. Engagement of the motor is accomplished by one of a number of methods, each of which utilizes an operator sensitive switch located within the toothbrush housing. One method merely requires the user to bring the brush head into contact with one or more teeth; here, the downward force on the brush head actuates the switch. Another method relies on the force generated by the user's grip to actuate the switch and start the motor. Yet another method involves the use of sensors in the handle such that the presence of the user's hand actuates the switch that engages the motor. The rotation of the motor, through various mechanical linkages, causes the brush head to oscillate, facilitating tooth cleaning.

In a preferred embodiment, the toothbrush has a two-piece housing in which most of the components are located. The housing contains a handle portion and a head portion, connected by a neck portion. The handle portion contains a compartment for a plurality of batteries, held in place and electrically connected by an end cap. Also within the handle portion is a first switch, having an "off" position and an "automatic" position.

A plurality of gears are operatively connected between the motor and a connecting arm. A spur gear, connected to the motor shaft, drives a ring gear which has an integral crank pin. A connecting arm is operatively connected between the crank pin and a shaft, the shaft being located substantially within the neck portion. In operation, this mechanism resembles a typical slider crank.

One end of the shaft is located in the head portion of the housing, and is operatively connected to a pinion which is attached to a brush head shaft located on the base side of the brush head. The pinion interfaces with a rack located within the head portion of the housing, thereby facilitating movement of the brush head.

In the preferred embodiment, a second switch is located substantially within the neck portion of the housing. This switch is characterized by two contact plates. The contact plates are not normally electrically connected; this keeps the electric circuit open. When a force is exerted on the brush head—e.g., when the brush head is in contact with the user's teeth—the two contact plates electrically connect, the circuit is closed, and the motor is engaged.

In an alternative embodiment, the second switch is located in the handle portion of the toothbrush. Here, the user squeezes a compressible portion of the handle, thereby closing the second switch. Different types of switches can be employed for this purpose, but the end result is the same. The motor will not rotate and the brush head will not move until the user squeezes the handle and actuates the second switch.

Another embodiment of the present invention also places the second switch in the handle portion; however, in this embodiment, sensors on the outside of the handle detect the presence of the user's hand. Hence, the user need not apply a gripping force to the handle to actuate this switch, rather, mere contact with the sensors closes the switch and completes the circuit.

In each of these embodiments, the first switch can be a three-position switch instead of the two-position switch described above. The use of a three-position switch adds as an option, a continuous "on" mode of operation. That is, the toothbrush could still be used in an "automatic" mode, or turned off completely, but the addition of the continuous "on" mode of operation would allow the toothbrush to be used in the manner of conventional motorized toothbrushes.

BRIEF DESCRIPTION OF THE DRAWINGS

FIG. 1 shows a simplified descriptive side view of an electric toothbrush in accordance with the present invention.

FIG. 2 shows a simple wiring schematic for the toothbrush shown in FIG. 1;

FIG. 3 shows an exploded view of the toothbrush shown in FIG. 1;

FIG. 4 shows a fragmentary sectional view of an alternative embodiment of the present invention;

FIGS. 5A and 5B show Detail A of FIG. 4;

FIG. 6 shows a plan view of the toothbrush shown in FIG. 4.

FIG. 7 shows a plan view of a third embodiment of a toothbrush in accordance with the present invention;

FIG. 8 shows a fragmentary sectional view of a fourth embodiment of the present invention;

FIG. 9 shows a fragmentary sectional view of a fifth embodiment of the present invention;

FIG. 10 shows a descriptive side view an a sixth embodiment of the present invention;

FIG. 11 shows a simple wiring schematic for the toothbrush shown in FIG. 10;

FIG. 12 shows a simple wiring schematic that can be used with any of the various toothbrush embodiments.

DETAILED DESCRIPTION OF THE PREFERRED EMBODIMENT

FIG. 1 shows a simplified descriptive side view of an electric toothbrush 10 in accordance with the present invention. Switch button 12 slides into one of two positions: "off" or "automatic". While in the automatic mode, motor 14 is engaged only when a force (F) is exerted on the brush head 16. This force causes a slight movement of the brush head 16 in the direction of the force. Because of this movement, a switch 18 is actuated, an electric circuit is completed, and current flows from batteries 20 to motor 14. The motor 14 transmits power to brush head 16 through a series of mechanical linkages, shown in detail in FIG. 3.

FIG. 2 shows a simple wiring schematic 30 of a circuit for the toothbrush shown in FIG. 1. Motor 32 is electrically connected between a power source 34 and a switch 36. When switch 36 is in the "off" position, the circuit is open and there is no voltage across motor 32. When switch 36 is in the "automatic" position, control of motor 32 is transferred to switch 38. While operating in the automatic mode, the motor 32 is only engaged when a force (F) is applied to switch 38. Switch 38 can be located in various locations within the toothbrush housing, such as in the handle or under the brush head.

FIG. 3 shows an exploded view of an electric toothbrush 50 in accordance with the present invention. A two-piece housing comprises a bottom housing 52 and a top housing 54. The housing has a handle portion 56, a neck portion 58, and a head portion 60. Within the handle portion 56 is a battery compartment 62. Batteries 64A, 64B are located within the battery compartment 62 and are electrically connected to each other by a battery connector 66A, 66B. The batteries 64A, 64B and battery connector 66A, 66B are held in place by an end cap 68.

Also within the handle portion 56 are battery plates 70 and 72 which connect to the positive 74A and negative 74B battery terminals, respectively. Switch button plate 76, is actuated using switch button 78 and switch cover 80. To facilitate use of the toothbrush in the automatic mode, a first contact plate 82 and a second contact plate 84 are located substantially within the neck portion of the housing. First contact plate 82 is electrically connected to switch button plate 76 via a first wire 86, and second contact plate 84 is electrically connected to negative battery plate 72 via a second wire 88.

When switch button 78 is in the "off" position, switch button plate 76 does not contact negative terminal 74B. When switch button 78 is in the "automatic" position, switch button plate 76 is in contact with negative terminal 74B, but not the negative battery plate 72. For current to flow to motor 74, when switch button 78 is in the automatic position, it is therefore necessary for first contact plate 82 and second contact plate 84 to be electrically connected.

Motor 74 is mounted inside handle portion 56 by means of motor mount 90. When current flows to motor 74, motor shaft 74C rotates, causing rotation of spur gear 92 which is mounted on motor shaft 74C. Spur gear 92 meshes with ring gear 94 which is provided with an eccentric crank pin 95. Crank pin 95 is operatively connected to a pivot on the first end of connecting arm 96. The second end of connecting arm 96 is pivotally connected to shaft 98, which is held in alignment by bearing 100. Electrical components are protected from contact with liquid by seal 102. In operation, as ring gear 94 rotates, eccentric crank pin 95 and the first end of connecting arm 96 rotate. This causes the second end of the connecting arm 96 and shaft 98 to translate axially in a typical slider crank manner.

Pinion 104 is operatively connected to shaft 98 and is attached to brush head shaft 106A. Rack 108 is securely mounted inside the head portion 60. As shaft 98 reciprocates, the interaction of pinion 104 and rack 108 causes brush head 16 to translate and rotate simultaneously. Brush head shaft 106A is integrally connected to brush head base 106B. Brush head bristles 106C are mounted on brush head base 106B, on the side opposite brush head shaft 106A.

Axial pressure on brush head bristles 106C causes a deflection of shaft 98 in the direction of the bottom housing 52. Shaft 98, in constant contact with plate 84, then moves a short distance until it also contacts plate 82; the two contact plates are thereby electrically connected. The electrical connection of the first contact plate 82 with the second contact plate 84, has no effect if switch button 78 is in the "off" position. However, when switch button 78 is in the "automatic" position, the electrical connection of the two contact plates completes the electric circuit that allows current to flow to motor 74. This means that when switch button 78 is in the "automatic" position, motorized movement of brush head 106 is predicated upon an axial force being applied to brush head 16.

Referring to FIG. 4, an electric toothbrush 150 is shown in accordance with an alternative embodiment of the present invention. Switch button 152 slides into one of two positions: "off" or "automatic". While in the automatic mode, motorized movement of brush head 154 occurs only when a force (F) is exerted on the compressible portion 156 of the tooth brush handle 158. This force causes magnet 160 to move in close proximity to switch plates 162. When magnet 160 gets within a critical distance of switch plates 162, the plates contact each other, thereby engaging the drive motor (not shown).

The magnetic switch mechanism shown in FIG. 4 in circle A, is shown in detail in FIGS. 5A and 5B. Normally, the switch is open; that is, magnet 160 is far enough away from magnetic plate 162A such that non-magnetic plate 162B does not contact plate 162A. After force (F) is applied to the compressible portion 156 of the toothbrush handle 158, and the distance between magnet 160 and magnetic plate 162A drops below the minimum critical gap 164, plate 162A is drawn toward magnet 160 such that it contacts plate 162B.

FIG. 6 shows a plan view of toothbrush 150 with a one-piece compressible portion 156. A third embodiment, shown in FIG. 7, uses a two-piece compressible portion. Here, toothbrush 170 has a two-piece compressible portion made up of rigid portion 172 and non-rigid portion 174, which is attached to toothbrush handle 176.

Turning to FIG. 8, a fourth embodiment is shown. Again, an electric toothbrush handle 200 contains a compressible portion 202. As in the preferred embodiment, magnet 204 is located beneath the compressible portion 202. Here however, the switch plates have been replaced with a Hall effect sensor 206. Application of force (F) to compressible portion 202 causes the distance between the magnet 204 and the Hall effect sensor 206 to decrease. When this distance is small enough, current flows through the Hall effect sensor 206 and the motor is engaged.

FIG. 9 shows a fifth embodiment of the present invention. Electric toothbrush handle 220 contains compressible portion 222. Below the compressible portion 222 are two contact plates 224 and 226. Application of force (F) to compressible portion 222 causes the two contact plates to electrically connect, thereby completing an electric circuit and engaging the toothbrush motor.

Referring to FIG. 10, an electric toothbrush 240 is shown in accordance with a sixth embodiment of the invention. In this embodiment, the mere presence of the user's hand on the handle causes movement of the brush head. In this figure, sensors 242 are located on the toothbrush handle. Typically a capacitive sensor would be used in this embodiment to allow the presence of the user's hand to close a switch in the handle, thereby engaging the motor.

An electric circuit for this embodiment is shown in FIG. 11. Here, switch 250 has two positions: "off", in which the circuit is open and no current can flow from power source 252 to motor 254, and "automatic", in which control of motor 254 is transferred to switch 256. While in the automatic mode, the presence of the user's hand on the toothbrush handle will engage tactile sensors 258. This causes switch 256 to close, and allows current to flow to motor 254.

Finally, FIG. 12 shows a simple wiring schematic 300 of a circuit configuration applicable to any of the embodiments described above. The button (shown as 12 in FIG. 1), now actuates a switch that has three positions instead of two. Turning back to FIG. 12, this switch is shown as 302. When switch 302 is in the "off" position, circuit 304 is open and there is no voltage across motor 306. When switch 302 is in the "on" position, circuit 304 is closed and there is a continuous voltage across motor 306. Finally, when switch 302 is in the "automatic" position, control of the motor 306 is transferred to circuit 308. Switch 310 closes circuit 308 only upon application of a force (F) to switch 310. Hence, when switch 302 is in the "automatic" position, current will flow from power source 312 to motor 306 only as long as a force (F) is applied to switch 310. Removal of force (F) opens circuit 308, thereby disengaging motor 306.

While these embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. An electric toothbrush comprising:
   a substantially hollow body having a head portion and a handle portion connected by a neck portion;
   a motor located within the handle portion;
   a first switch located within the handle portion having an open position and a closed position, wherein the open position prevents operation of the motor and the closed position facilitates automatic operation of the motor;
   a moveable brush head having a plurality of bristles;
   a drive assembly operatively connected between the motor and the moveable brush head; and
   a second switch located within the body, wherein actuating the second switch causes operation of the motor when the first switch is in the closed position, and wherein the second switch is automatically closed when the toothbrush is used by an operator, the second switch including a pair of contact plates located substantially within the neck portion, and wherein a force imparted to the moveable brush head in use, causes the contact plates to electrically connect, thereby actuating the second switch.

* * * * *